United States Patent [19]
Decker

[11] 4,453,925
[45] Jun. 12, 1984

[54] TAMPON INSERTION DEVICE
[75] Inventor: William D. Decker, Darlington, S.C.
[73] Assignee: Sonoco Products Company, Hartsville, S.C.
[21] Appl. No.: 348,341
[22] Filed: Feb. 12, 1982
[51] Int. Cl.³ .............................................. A61F 15/00
[52] U.S. Cl. ................................................... 604/14
[58] Field of Search ............................. 604/11, 14–18, 604/310–311, 275; 493/404, 396, 59, 156, 157, 160; 425/291–296

[56] References Cited
U.S. PATENT DOCUMENTS
3,581,744  6/1971  Voss ...................................... 604/14
4,197,788  4/1980  Wharton, Jr. ......................... 493/59

Primary Examiner—C. Fred Rosenbaum
Assistant Examiner—Sherri E. Vinyard
Attorney, Agent, or Firm—Dennison, Meserole, Pollack & Scheiner

[57] ABSTRACT

A tampon insertion device comprising an elongated tube of spirally wound laminated paper construction provided with a domed insertion end defined by a series of generally hemispherically cupped petals. The petals are formed in a generally triangular configuration through the removal of tube material by appropriate punch and die apparatus. The insertion end of the tube, preferably prior to the defining of the petals in the tube end, is provided with longitudinal scores oriented to locate a single score extending centrally along each of the formed petals. Additionally, multiple circumferential scores are provided about the insertion end of the tube whereby each formed petal will incorporate multiple transversely extending scores. In longitudinally and circumferentially scoring the insertion end, the tube, normally mounted on an inner stabilizing mandrel, is manipulated to introduce the insertion end through an annular die having inwardly directed circumferentially spaced scoring blades corresponding in number to the number of petals to be formed. The mandrel mounted tube next positions the longitudinally scored insertion end adjacent the outer periphery of a roller die with multiple projecting scoring blades for effecting formation of the circumferential scores, either the mandrel supported tube or the roller die being driven with the other freely rotating therewith. The petals are subsequently defined and, utilizing a hemispherically shaped concave female die, formed into the domed configuration.

21 Claims, 21 Drawing Figures

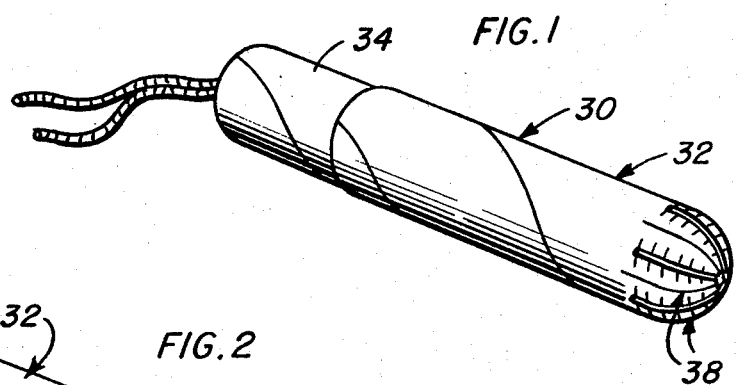
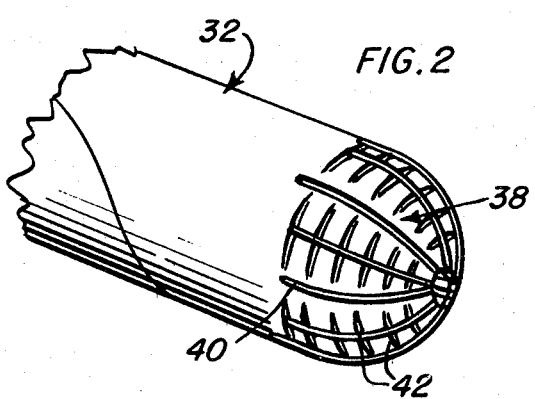
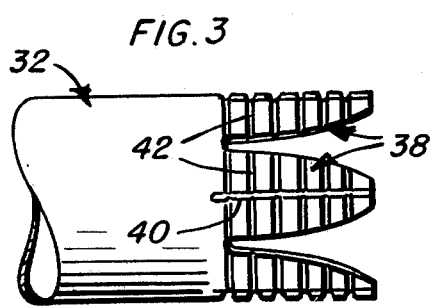
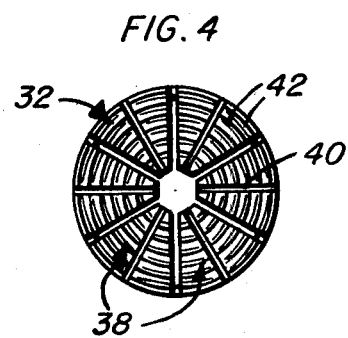
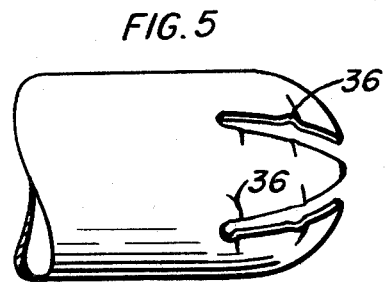
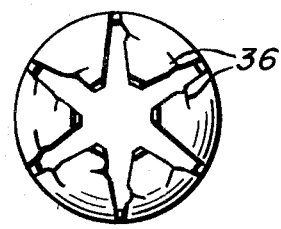

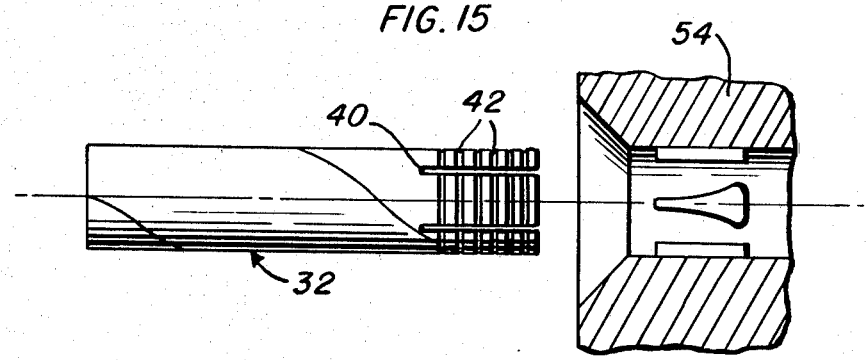
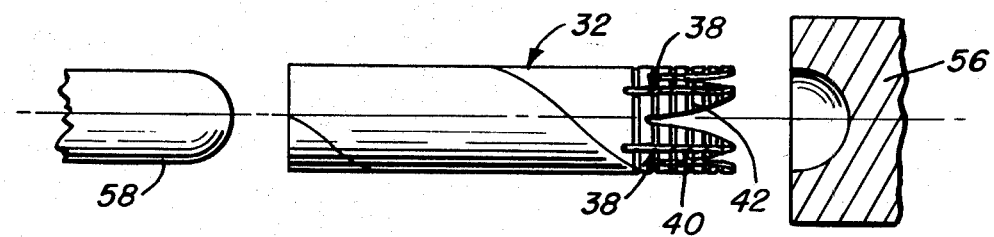
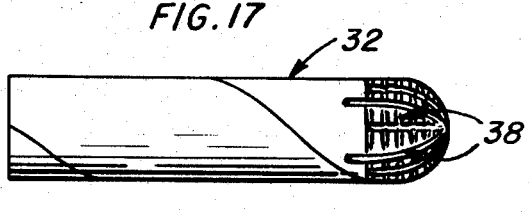
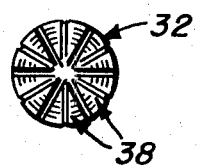
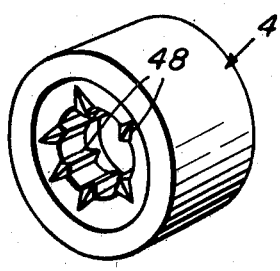
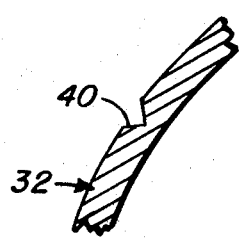
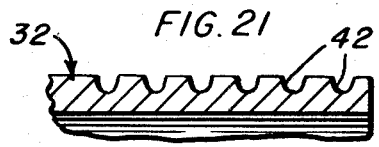

TAMPON INSERTION DEVICE

BACKGROUND OF THE INVENTION

The invention herein broadly relates to tampons, particularly catamenial tampons, and is more specifically directed to tampon inserters or insertion devices.

The increased acceptance of cantamenial tampons as a viable replacement for sanitary napkins has been due to a variety of factors, not the least of which is the ease of insertion. While insertion can be done through a direct placement of the absorbent tampon using one's hand, the preferred manner, and the manner which has most contributed to the acceptance of catamenial tampons, is by the use of a tampon applicator or insertion device. Such applicators basically comprise an outer insertion tube having a leading end, a tampon positioned within the insertion tube immediately inward of the leading end, and a pusher or ejection tube inserted within the insertion tube immediately behind the tampon for a forward discharge of the tampon through the leading end of the insertion device. As will be appreciated, the insertion device is itself introduced into the vagina or other body orifice and withdrawn along with or subsequent to the forward discharge of the tampon.

Inserters or applicators of the above described type preferably incorporate a domed or tapered leading end defined by an inward folding of the leading end of the insertion tube, normally by formation of individual triangular segments which are inwardly deformed to the desired configuration. Such applicators, or more particularly the tubes thereof, are formed of a variety of materials, particularly thermoplastics such as polyethylene and laminated paper or cardboard. As will be appreciated by those familiar with the art, much patent activity has been directed to tampon applicators or inserters such as those referred to above. In this regard, attention is directed to U.S. Pat. No. 3,895,634, issued July 22, 1975, to Berger et al, for its detailed review of the general state of the art as it existed at the time of issuance of that patent.

Similar disclosures relating to tampon applicators of the general type with which we are herein concerned will also be noted in the following patents:

U.S. Pat. No. 2,178,840; Lorenian; Nov. 7, 1939
U.S. Pat. No. 3,358,354; Voss; Dec. 19, 1967
U.S. Pat. No. 3,433,225; Voss; Mar. 18, 1969
U.S. Pat. No. 3,830,236; Hanke; Aug. 20, 1974

The plastic applicators, that is those formed of polyethylene or the like, have, from a structural standpoint, been quite acceptable insofar as the formation of a multi-petal tip or leading end. This probably arises from the flow characteristics of the plastic and the ability thereof to mold into the desired configuration. However, no one has as yet been able to come forth with a truly successful formation of such inserters utilizing an insertion tube of laminated paper, cardboard or the like. Basically, problems arise in attempting to form the normally triangularly configured segments into a smooth permanent domed configuration that is strong enough to withstand insertion forces yet flexible enough to permit easy ejection of the tampon therethrough. Heretofore, efforts to define a tapered or domed leading end on paperboard tubes has been less than successful in that series of wrinkles occur along the outside edges of each petal, and the petals will not normally maintain the desired smooth domed configuration In this regard, upon removal of the insertion tube from the forming die, used to shape the domed leading end, the petals tend to relax and spring-back toward the original cylindrical configuration of the tube, thus creating gaps between the edges of the petals as well as the enlarged gap at the extreme leading end of the petals. This tendency to spring-back, that is the inability of the paper petals to maintain the domed configuration, is basically due to the nature of the paperboard tube itself which resists reshaping efforts. Accordingly, notwithstanding the significant advantages which might be found in the use of paper tubes, including ease of formation, minimal expense, ready accommodation to insertion and removal with minimal frictional resistance or skin surface irritation, and the like, the paper tube has not received the degree of acceptance which might be achieved were it possible to more perfectly configure the domed leading end.

SUMMARY OF THE INVENTION

The present invention proposes a laminated paper insertion tube, and a related system for the formation of the tube, which avoids the problems heretofore associated with such paper tubes. As disclosed herein, the domed leading end is formed to a degree of perfection equal to or greater than that previously achieved only in molded plastic tubes, avoiding all of the defects, including wrinkling, spring-back, and the like, normally associated with paper tubes.

Basically, the tube of the present invention, preferably formed of multiple plies of spirally wound laminated paper with an outer ply of thick varnish coat or polyethylene coated white paper, has the leading end thereof defined by multiple generally triangularly configured petals adapted for inward doming utilizing, primarily, a male mandrel received within the tube and an external female die. The male mandrel has a forward convex end while the female die is heated and provided with a hemispherically configured concave recess therein.

The petals themselves are particularly provided with means to facilitate the doming thereof, assure the doming of the petals without edge or body wrinkles, and substantially contribute to the maintaining of the petals in the domed configuration. Specifically, each petal is provided with a longitudinal score therein extending from the peak rearwardly to, and preferably slightly beyond, the base of the petal. In addition, each of the petals is provided with multiple transverse scores equally spaced from each other between the apex of the petal and the base. In each instance, the scores are in the external surface of the petal and compress the material thereof with little or no disruption of the interior surface of the petal. With the presence of these scores, the individual petals have been found to, when subjected to a doming operation, effectively assume a wrinkle-free "cupped" configuration which retains its formed shape upon removal from the forming die and which provides, in conjunction with the remainder of the petals, a perfectly configured leading end dome possessing improved strength to withstand insertion forces, while leaving each petal flexible enough to unfold and permit easy ejection of the tampon. It appears that the strengthening of the domed end, to withstand greater insertion forces than those to which a paper tube can normally be subjected, comes from the scores acting in the manner of a series of ribs reinforcing each petal in its "cupped" configuration which in turn allows the petals to work integrally as a smooth hemispherically shape to resist the forces. At the same time, the scores provide surface relief areas which appear to relieve forming stresses to avoid wrinkling.

In the actual forming procedure, the spirally wound tube is mounted on an elongated internal mandrel and the leading end thereof introduced through an annular die having a series of radially inwardly projecting sharp-pointed scoring blades which define the longitudinal scores, so positioned as to ultimately provide for the extension of a single longitudinal score along each petal.

The mandrel mounted tube is next manipulated to position the longitudinally scored leading end thereof into peripheral engagement with a roller die having multiple equally spaced scoring blades peripherally thereabout. Both the roller die and the tube are rotatably mounted whereby a driving of one or the other will effect a rotation of both and a scoring engagement of the blades with the leading end of the tube peripherally thereabout.

The longitudinally and circumferentially scored leading end is then subjected to a punching operation whereby the petals are defined by the removal of excess material therebetween. This punching operation may follow one or more of the procedures known in the art. However, regardless of the procedure followed care must be taken to form the petals to provide each petal with a longitudinal score line between the apex and base thereof. As an assurance of this relationship, it may be feasible to mount the annular die which defines the longitudinal scores immediately forward of the petal cutting apparatus, normally in itself consisting of a series of circumferentially spaced dies, with the alignment being such whereby the longitudinal scores and petal cutting will be performed as aligned sequential operations. With such a procedure, the circumferential scores will probably be formed prior to the formation of the longitudinal scores.

After formation of the scored petals, the petals will be deformed or molded into the desired domed configuration utilizing a heated concave female die into which the leading end of the petals are introduced, and an internal mandrel with a convex male end which acts to stabilize and guide the leading end of the tube during the doming operation.

Additional features and advantages residing in the details of construction, method of formation, and apparatus will become apparent as the invention is more fully herinafter described and claimed.

BRIEF DESCRIPTION OF THE DRAWINGS

FIG. 1 is a perspective view of a tampon inserter constructed in accordance with the present invention;

FIG. 2 is an enlarged view of the leading domed end of the insertion tube;

FIG. 3 is an elevational view of the insertion end subsequent to formation of the scored petals and prior to doming;

FIG. 4 is a face view of the domed end;

FIGS. 5 and 6 illustrate the prior art use of unscored petals on paper tubes and the resultant wrinkling, gapping, and the like encountered;

FIG. 15 is a side elevational view of the inserter tube with the leading end incorporating both the longitudinal scores and the circumferential scores, and aligned with a schematic representation of any appropriate punch apparatus used to define the individual petals;

FIG. 16 is a side elevational view of the tube with the petals defined, the tube aligning with a schematic representation of a female doming die;

FIGS. 17 and 18 are respectively a side view and an end elevational view of the completed inserter or insertion tube with the domed leading end;

FIG. 19 is a detailed view of the annular die utilized in the formation of the longitudinal scores;

FIG. 20 is a sectional detail through one of the longitudinal scores; and

FIG. 21 is a sectional detail through multiple ones of the circumferential or transverse scores.

DESCRIPTION OF THE PREFERRED EMBODIMENTS

Figure 7:
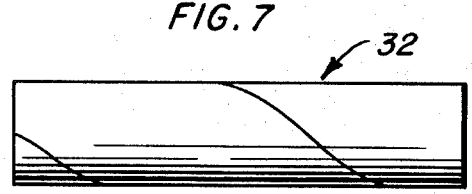
FIGS. 7 and 8 respectively illustrate an inserter tube, in side elevation and end elevation, prior to initiating the various petal forming steps.

Referring now more specifically to the drawings, reference numeral 30 designates a tampon insertion device formed in accordance with the present invention. This device, as in a conventional tampon insertion device, includes an outer insertion or inserter tube 32, an inwardly position absorbent tampon, not shown, and a smaller pusher or ejection tube 34 introduced through the following end of the insertion tube for a forward propelling and discharge of the tampon.

Of particular significance in regard to the present invention is the insertion tube 32. This tube 32 is to be formed of paper or cardboard, and preferably comprises a tube of spirally wound laminated paper construction. The tube, approximately three inches in length with an inside diameter of 0.625 inches and a wall thickness of 0.018 inches, will normally be formed of three plies, two body plies of 0.008 inch thick groundwood paper with one outer ply of 0.002 inch thick varnish coat or polyethylene coated white paper.

Figure 8:
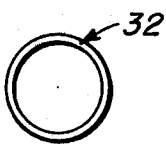

This basic spirally wound paper tube 32, prior to a defining of the leading end thereof for use as an insertion tube, is illustrated in FIGS. 7 and 8. Were this tube to be processed in the conventional manner of the prior art to define multiple arced petals, the resultant structure would be similar to that illustrated in the prior art figures of FIGS. 5 and 6. This construction, while obviously better than providing no doming whatsoever, is far from satisfactory due to the tendency for the petals to excessively gap-open both between adjacent petals and at the apexes thereof. Also, as clearly suggested in FIGS. 5 and 6, substantial bulging and wrinkling 36 occurs along the edges of the individual petals, particularly at the ply gaps in the spiral construction and at or near the base of each petal.

The present invention, utilizing the same basic spirally wound paper tube, effectively avoids the problems graphically illustrated in FIGS. 5 and 6. This is achieved, noting initially FIGS. 2 and 3, by the formation of the leading end petals, herein designated by reference numeral 38, with both longitudinally and transversely extending scores 40 and 42 respectively. Each petal 38 includes a single central score 40 extending longitudinally from the truncated apex of the petal 38 to a point slightly beyond the base of the petal. The scores 40, assuming a tube of the approximate dimensions referred to above, will be approximately 0.010 inches deep and 9/16 inches long.

The provision of such a longitudinal score along the center of each petal has been found to substantially contribute to elimination of the tendency for the petals 38 to relax and spring-back subsequent to a removal of the leading end of the tube 32 from the die apparatus used to define the domed configuration. As will be recognized, it is essential that in order to form a smooth substantially hemispherical dome each of the petals be cupped, that is both longitudinally and transversely curved, and that this configuration be maintained against any inherent tendency of the material of the petals to return to the original or unformed configuration.

The transverse scores 42, also of a constant 0.010 depth prior to cupping of the petals 38, perform multiple significant functions including contributing to the ability of the petals to maintain themselves into the desired formed domed configuration. Of equal importance is the fact that the circumferential scores eliminate the wrinkling problem normally encountered along the opposed edges of each petal when utilizing tubes formed of paper and the like. As will be appreciated from FIGS. 2 and 3, the transverse scores 42 in the cupped petals 38 are much less pronounced throughout the center of each petal, notwithstanding the constant depth of the scores 42 during the initial formation thereof, the scores 42 providing relief areas accommodating the slight degree of dimensional change in the outer surface during the cupping or doming operation.

With further reference to the transverse or circumferentially formed scores 42, while the number of such scores can vary, it is preferred that six be provided in equal longitudinally spaced relation to each other along the leading end of the tube 32 from the base of the petals 38 outward.

Attention is now directed to FIGS. 7 through 18 in connection with the procedures followed and the apparatus used in the formation of the insertion tube 32.

As previously indicated, the basic tube, illustrated in FIGS. 7 and 8, is preferably formed of spirally wound laminated paper, is approximately three inches in length and includes a wall thickness of approximately 0.018 inches.

Figure 9:
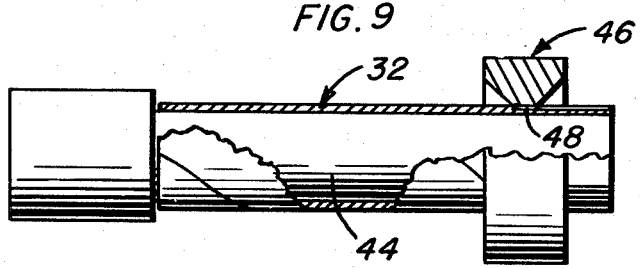
FIGS. 9 and 10 are respectively side and end elevational views, with portions broken away for purposes of illustration, of introduction of a mandrel mounted tube through an annular die to define the longitudinal scores.
Figure 10:
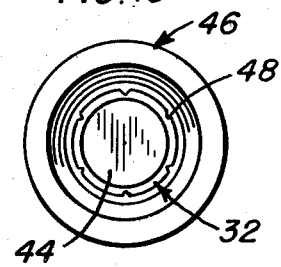
Figure 11:
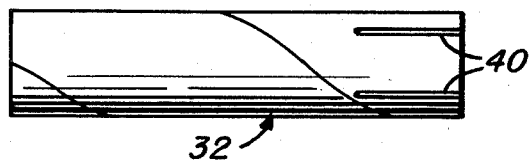
FIGS. 11 and 12 respectively illustrate, in side elevation and end elevation, the inserter tube after formation of the longitudinal scores.
Figure 12:
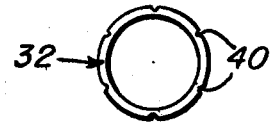

This tube 32, noting FIGS. 9 and 10, is received over an elongated mandrel 44 which closely conforms to the interior of the tube 32 and is used to stabilize and guide the tube 32 as the leading end thereof moves through an annular scoring die 46 having multiple, six in the illustrated example, inwardly directed sharp blades 48 provided about the inner periphery at equally spaced points to correspond with the midpoints of the petals 38 to be subsequently formed. The blades 48 are to be sharp pointed, typically defining a 60° angle, and of a length so as to provide a longitudinal score 40 of an approximate depth of 0.010 inches. It is contemplated that the relationship between the material of the tube and the blades be such whereby the longitudinal scores 40 are formed without breaking the protective surfacing or coating of the tube. FIGS. 11 and 12 illustrate the tube 32 with the leading end longitudinally scored and both the mandrel 44 and die 46 removed. FIG. 19 is an enlarged view of the annular die 46 more specifically detailing the features thereof. FIG. 20 is an enlarged cross-sectional detail through one of the longitudinal scores 40.

Figure 13:
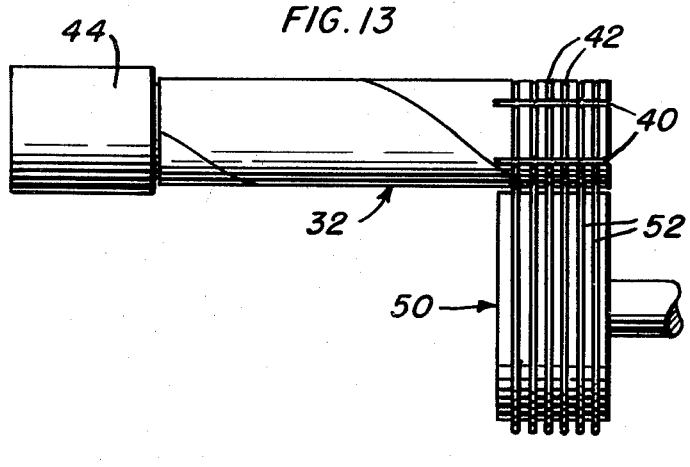
FIGS. 13 and 14 respectively illustrate, in side elevation and end elevation, the mandrel mounted tube cooperating with the roller die in the formation of the circumferential scores about the leading end.
Figure 14:
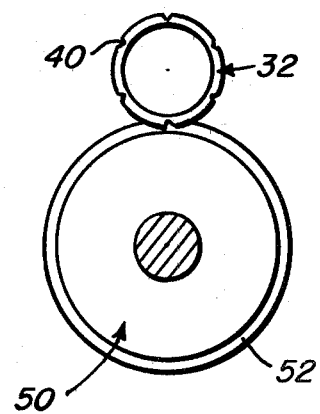

FIGS. 13 and 14 are directed to circumferentially scoring the leading end of tube 32 to define the transverse scores 42. Basically, the tube 32, again mounted on an appropriate mandrel 44, is oriented to position the periphery of the leading end against the periphery of a roller die 50, shaft mounted for rotation. The roller die 50 has, across the face width thereof, multiple projecting annular scoring blades 52, six such blades being provided in the illustrated example. These scoring blades are preferably 1/32 inch wide with a 1/64 inch point radius and are positioned 5/64 inches apart center to center line. As with the blades 48, the blades 52 define scores approximately 0.010 inches in depth. The circumferential scores will preferably be formed by a rotational driving of the tube 32 with the scoring die 50, bearing supported, freely rotating in contact with the leading end portion of the tube 32 to define the continuous circumferential scores 42. Alternatively, the circumferential scoring of the tube can be effected by a driving of the scoring die 50 with the tube rotating freely on the support mandrel 44. FIG. 21 illustrates several of the circumferential or transverse scores 42 in enlarged detail.

FIG. 15 illustrates the completely scored tube 32 aligned with a schematic representation of an appropriate punching apparatus 54 which removes selected portions of the leading end of the tube 32 to define the petals 38. The tube with the formed petals will be noted in FIG. 16. As will be appreciated, the opposed side edges of the petals are slightly arcuate to appropriately lie adjacent the edges of the adjoining petals upon a cupping of the petals into a domed configuration with minimal spacing therebetween. In addition, the outer or apex ends of the petals 38 are truncated to avoid any possible irritating points.

FIG. 16 also schematically illustrates, in alignment with the leading end of the tube 32, a heated female die 56 having a concave or hemispherical seat therein utilized in the cupping of the petals and the doming of the leading end. This operation will also normally utilize a male mandrel-like mold member 58 within the tube and having a convex leading end generally conforming to the hemispherical seat to form the dome configuration therebetween.

Inasmuch as it is particularly significant that the longitudinal scores 40 be properly registered with the petals 38, it is contemplated that, as a variation in the procedure above described, the longitudinal scoring die 46 can be mounted on the face of the petal punch 54 whereby the longitudinal scores can be defined as the tube is inserted into the punching apparatus. As will be appreciated, this will necessitate a formation of the circumferential scores either prior to the formation of the longitudinal scores or subsequent to the formation of the petals.

The completed insertion tube 32 is illustrated in FIGS. 17 and 18. The cupped configuration of the individual petals, and correspondingly, the domed configuration of the entire leading end of the tube, are formed without edge wrinkling or buckling, and without any tendency to relax, "spring-back" or gap when removed from the forming die 56. These advantages are derived specifically from the scoring of the petals in the manner detailed. As will be best appreciated from the enlarged views of FIGS. 2 and 3, the hemispherical arcing of the petals 38 in a longitudinal direction cause a relative extension or elongation of the outer surface of the petals which is particularly accommodated by the transverse scores 42. These scores 42 typically substantially disappear along the central portion of each of the petals as the longitudinal arc of the individual petals is accommodated, thus enhancing the smooth outer surface of the leading end. These transverse scores also provide a major contribution in eliminating edge wrinkling. The longitudinal scores effectively enhance the ability of the individual petals to transversely curve or cup and retain the cupped configuration.

The provision of the scores has also been found to strengthen the domed leading end in that the scores, compressing the paper material at the leading end, provide what amounts to a series of reinforcements which enable the domed end to withstand greater insertion forces as the petals work integrally.

While six petals have been illustrated, and are considered the preferred number, it will be appreciated that the number of petals can vary. Similarly, while six transverse scores are considered preferred, a variation in the number of scores is also contemplated within the scope of the invention.

As will be appreciated, the scores 40 and 42 are in the nature of grooves defined in the outer surface of the tube, and specifically in the outer surfaces of the individual petals. These scores simultaneously provide both strengthening lines and relief areas to accommodate the compound curvatures to which the petals are subjected.

The foregoing is considered illustrative of the principles of the invention. As variations and modifications will be recognized, it is not desired to limit the invention to the exact construction and procedures described. Rather, all suitable modifications and equivalents may be resorted to, falling within the scope of the invention as presented.

I claim:

1. In a tampon insertion device, a cylindrical insertion tube of paperlike material, said tube having a leading end comprising a plurality of generally triangular petals inwardly cupped into a leading domed configuration, each of said petals comprising inner and outer surfaces, opposed side edges, an apex and a base, the side edges of each petal being independent of the side edges of adjacent petals, and a plurality of nonirritating relief areas defined in the outer surface of each petal, said relief areas accommodating stresses developed in the inward cupping of the individual petals, said petal outer surfaces with said relief areas defining an outer surface of the domed configuration which is substantially without stress-developed surface disruptions.

2. The device of claim 1 wherein said relief areas comprise a plurality of scores in the outer surface of each of said petals.

3. The device of claim 2 wherein said scores extend transversely inward from the opposed edges of each of said petals.

4. The device of claim 3 wherein one of said scores extends along the base of each of said petals with the remaining scores on the petal being in upwardly spaced relation thereto and to each other.

5. The device of claim 4 including a longitudinal score along each of said petals in general alignment with the apex thereof.

6. The device of claim 5 wherein the longitudinal score in each petal extends along the full height thereof.

7. The device of claim 6 wherein said insertion tube is formed of multiple laminated plies.

8. The device of claim 2 including a longitudinal score along each of said petals in general alignment with the apex thereof.

9. The device of claim 1 wherein said insertion tube is formed of multiple laminated plies.

10. For use in the formation of a tampon insertion device, an elongated cylindrical tube of paperlike material, said tube including a leading end defined by a plurality of separate longitudinally projecting petals positioned in spaced relation about said tube for inward convergence into a domed configuration, each of said petals including an outer surface, each petal outer surface having multiple recessed relief areas defined therein for accommodation of stresses and an avoidance of outer surface disruption upon an inward convergence of said petals into a smoothly domed configuration with a nonirritating outer surface defined by the petal outer surfaces.

11. The device of claim 10 wherein said relief areas comprise a plurality of scores in the outer surface of each of said petals.

12. The device of claim 11 wherein said petals have opposed edges, at least selective ones of said scores extending inwardly of said opposed edges.

13. The device of claim 12 wherein each of said petals is of a generally triangular configuration including a base and an apex, one of said scores extending along the base of each of said petals with additional scores in upwardly spaced parallel relation thereto and to each other along each of said petals, and a longitudinal score centrally through each petal generally aligned with the apex thereof.

14. The device of claim 13 wherein said tube is formed of multiple laminated plies.

15. The device of claim 10 wherein the relief areas defined in the outer surface of each of said petals include multiple scores, one of which is longitudinally directed centrally of each petal.

16. In the formation of a tampon insertion tube with a domed leading end, the steps of providing a cylindrical elongated tube of paperlike material and having a leading end, grooving the outer surface of said leading end of said tube to provide nonirritating stress relieving areas therein, severing said leading end into a plurality of separate longitudinally extending petals, each incorporating at least portions of said grooves, and forming said petals into a domed configuration.

17. The method of claim 16 wherein the grooving of the outer surface of the leading end of said tube includes the formation of circular grooves thereabout.

18. The method of claim 17 wherein the grooving of the outer surface of the leading end of said tubes includes the formation of longitudinal grooves therein.

19. The method of claim 18 wherein the leading end is initially longitudinally grooved and subsequently circumferentially grooved.

20. The method of claim 18 wherein said leading end is longitudinally grooved by projection of said leading end through an annular die with multiple inwardly directed die blades which engage the outer surface of said end.

21. The method of claim 20 wherein said leading end is circumferentially grooved by engagement of the periphery of the leading end of the tube against the blade carrying periphery of a rotatable die, and rotating said leading end relative to said die.

* * * * *